United States Patent [19]
Pfleiderer et al.

[11] Patent Number: 5,902,810
[45] Date of Patent: May 11, 1999

[54] PTERIDINE DERIVATIVES AS NO SYNTHASE INHIBITORS

[75] Inventors: Wolfgang Pfleiderer, Konstantz; Harald Schmidt, Dettelbach, both of Germany; Rainer Henning, Shibuya-ku, Japan

[73] Assignee: Hoechst Aktiengesellschaft, Frankfurt am Main, Germany

[21] Appl. No.: 08/737,657

[22] PCT Filed: May 6, 1995

[86] PCT No.: PCT/EP95/01731

§ 371 Date: Feb. 18, 1997

§ 102(e) Date: Feb. 18, 1997

[87] PCT Pub. No.: WO95/31987

PCT Pub. Date: Nov. 30, 1995

[30] Foreign Application Priority Data

May 24, 1994 [DE] Germany ............................ 44 180 96

[51] Int. Cl.$^6$ ...................... A61K 31/495; C07D 475/04; C07D 475/08

[52] U.S. Cl. ............................ 514/249; 544/258; 544/259; 544/260; 544/261

[58] Field of Search ..................... 544/258, 259, 544/260, 261; 514/249

[56] References Cited

U.S. PATENT DOCUMENTS

4,079,056  3/1978  Piper et al. .......................... 260/251.5

FOREIGN PATENT DOCUMENTS

| 2075346 | 6/1993 | Canada . |
|---|---|---|
| 0108890 | 5/1984 | European Pat. Off. . |
| 154 173 | 9/1985 | European Pat. Off. . |
| 290 819 | 11/1988 | European Pat. Off. . |
| 6-056669 | 3/1994 | Japan . |
| 9414780 | 7/1994 | WIPO . |
| 9532202 | 11/1995 | WIPO . |

OTHER PUBLICATIONS

Traub, Hermann M., "Synthese Und Eigenschaften Von Tetrahydrobiopterin–Analogen Potentielle Cofaktoren Für Biologishe Hydroxylierungen", Dissertation for the University of Konstanz, May 1987.

Montgomery et al., Analogues of Methotrexate, Journal of Medicinal Chemistry, vol. 22, No. 7, pp. 862–868, Jul. 1979.

Nasir et al., Coope(I) and Copper(II) Complexes of New Chelating Pterins, Journal of the American Chemical Society, vol. 114, No. 6, pp. 2264–2265, Mar. 1, 1992.

Slavik et al., CAS Printout, 1972.

Sokoloski et al., Induction of HL–60 Leukemia Cell Differentiation By Tetrahydrofolate Inhibitors of De Novo Purine Nucleotide Biosynthesis, Cancer Chemotherapy Pharmacology, vol. 28, No. 1, pp. 39–44, 1991.

Taylor et al., Pteridines. XXXVIII. Synthesis of Some 2,4–Diamino–6–Substituted Methylpteridines. A New Route To Pteroic Acid, Journal of Organic Chemistry, vol. 40, No. 16, No. 16, pp. 2347–2351, Aug. 8, 1975.

Netzer, T et al. British J. Pharmacology (1992), 106,222–6.

Werner–Falmayer et al, J. Exp. Med, vol. 172, Dec. 1990, 1599–1607.

Nakayame Don K. et al.,Am. Physiological Soc. (Apr. 1994) vol. 260 L455–460.

Schoedon, G. et al., Biochemical & Biophysical Research Comm., vol. 199 No. 2, Mar. 15, 1994 pp. 504–510.

Sakai, Naoki et al., $BH_4$ and NO Synthesis, vol. 48(1) pp. 6–10, 1993.

Gunther Konrad et al., Chem Ber., 103, (1970) pp. 722–734.

Jorens, Philippe G. et al., Br. J. Pharmacol, (1992), 107, 1088–1091.

Primary Examiner—Mukund J. Shah
Assistant Examiner—Brenda Coleman
Attorney, Agent, or Firm—Finnegan, Henderson, Farabow, Garrett & Dunner, LLP

[57] ABSTRACT

The present invention relates to the use of pteridine derivatives of the formula I

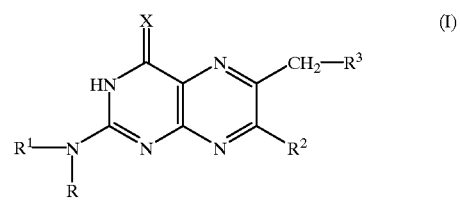

in which X is O, NH or N—$(C_{1-C5})$-alkanoyl, $R^3$ is the radical —$OR^4$, —$NR^5R^6$ or —$S(O)_mR^7$, and R, $R^1$, $R^2$, $R^4$, $R^5$, $R^6$, $R^7$ and m have the meanings given in claim 1, which are nitric oxide synthase inhibitors, for the treatment of diseases which are caused by an increased nitric oxide level.

13 Claims, No Drawings

PTERIDINE DERIVATIVES AS NO SYNTHASE INHIBITORS

This application is a 371 of PCT/EP95/01731 filed May 6, 1995.

The present invention relates to pteridine derivatives of the formula I

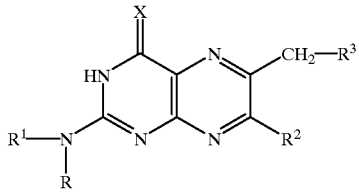

which on account of their ability to modulate endogenous nitric oxide production are useful pharmaceuticals for the prevention and control of states which are characterized by a disturbed nitric oxide level.

Nitric oxide (NO) plays an important part in all sorts of physiological processes (see, for example, R. Henning, Nachr. Chem. Tech. Lab. 41 (1993), 413; H. H. H. W. Schmidt et al., Biochim. Biophys. Acta 1178 (1993), 153). It has, for example, a relaxing effect on the smooth vascular musculature and in this way is substantially involved in the regulation of blood pressure. It controls blood clotting via inhibition of platelet aggregation, and it is involved, for example, as a neurotransmitter in the brain in the building up of long-term memory. NO also functions as a messenger substance in the NANC nerves of the peripheral nervous system. The cytotoxic action of NO is utilized by macrophages for defense against infection.

Endogenous NO is formed from arginine with the aid of at least three different NO synthase isoenzymes (see, for example, J. F. Kerwin, Jr. and M. Heller, Med. Res. Rev. 14 (1994), 23). They differ with respect to their localization in the body, their regulability by $Ca^{2+}$/calmodulin and their inducibility by endotoxins and cytokines. The constitutive, calcium-dependent NO synthases are found, for example, in endothelium (Type III) and in the brain (Type I) and are involved there in the regulation of blood pressure and coagulation and in conduction processes. The cytokine-inducible, calcium-independent isoform (Type II) occurs in macrophages, smooth muscle cells and hepatocytes. It is able, over the long term, to produce relatively large amounts of NO and is held responsible for inflammatory processes and the cytotoxic activity of the macrophages.

A disturbed NO balance results in serious disorders and damage. Thus excessive formation of NO in septic or hemorrhagic shock leads to massive pathological blood pressure decreases. Excess NO production is involved in the formation of type 1 diabetes and atherosclerosis and also appears to be responsible for glutamate-induced neurotoxicity after cerebral ischemia. High NO concentrations can moreover lead to DNA damage as a result of deamination of cytosine. Examples of disorders which are caused indirectly or directly by a lack of endogenous NO are arterial high blood pressure, hemostasis disorders, coronary heart disease and erectile dysfunction.

The attempt to use modulation of NO production for the treatment of these syndromes has until now only been realized with the aid of arginine analogs (GB-A-2240041; WO-A-93/13055). Further potential NO synthase inhibitors discussed in the literature are N-iminoethylornithine (McCall et al., Br. J. Pharmacol. 102 (1991), 234), aminoguanidine (T. P. Misko et al., Eur. J. Pharmacol. 233 (1993), 119; EP-A-547588) and 7-nitroindazole (P. K. Moore et al., Br.J.Pharmacol. 108 (1993), 296).

Various pteridine derivatives occur in nature, and uses of pteridine derivatives as pharmaceutical active compounds have also been described. The cytostatic methotrexate is a pteridine derivative. EP-B-290819 discloses the use of pteridines, among them also those of the formula I in which $R^3$ is hydroxyl, for the treatment of cognitive pathologies. For investigations on NO synthase which considered mechanistic questions, until now hydrogenated pteridine derivatives were especially used (see, for example, Kwon et al. (J. Biol. Chem. 264 (1989), 20496) or Giovanelli et al. (Proc. Natl. Acad. Sci. USA 88 (1991), 7091)). Accordingly, tetrahydrobiopterin stimulates NO production and is a cofactor of No synthases. Stimulation of NO production was also found for 7,8-dihydrobiopterin. Hevel and Marletta (Biochemistry 31 (1992), 7160) report on an increase in NO synthase activity due to 6-methyl-5,6,7,8-tetrahydropterin. Nonhydrogenated pteridines, such as, for example, biopterin, pterin, folic acid or 6-hydroxymethylpterin, showed no significant effects in investigations of this type (Kwon et al., J. Biol. Chem. 264 (1989), 20496).

Surprisingly, it has now been found that pteridine derivatives of the formula I, in particular, have an inhibiting modulatory effect on endogenous NO production and are thus suitable as pharmaceuticals in diseases which are characterized by an excessive NO level.

The present invention relates to the use of pteridine derivatives of the formula I

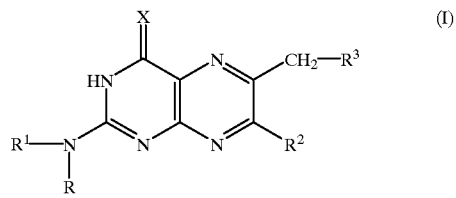

in which

X is O, NH or N—$(C_1$–$C_5)$-alkanoyl;

R is hydrogen and $R^1$ is hydrogen or $(C_1$–$C_5)$-alkanoyl or R and $R^1$ together with the nitrogen atom to which they are bonded form a dimethylaminomethyleneamino group;

$R^2$ is hydrogen, methyl, phenyl, hydroxyl, methoxy or amino;

$R^3$ is the radical —$OR^4$, —$NR^5R^6$ or —$S(O)_mR^7$, where m is the numbers 0, 1 or 2;

$R^4$ is hydrogen, $(C_1$–$C_{10})$alkyl, cyclohexyl, benzyl, phenyl which is unsubstituted or substituted by chlorine or the radical —$COR^8$, aminocarbonylmethyl which is unsubstituted or substituted on the nitrogen by one or two identical or different $(C_1$–$C_4)$-alkyl radicals, 2-methoxyethyl, the (2,2-dimethyl-1,3-dioxolan-4-yl) methyl radical or the radical —$COR^9$;

$R^5$ is hydrogen, methyl, ethyl, 2-hydroxyethyl, 2-chloroethyl, benzyl, pyridylmethyl, phenylethyl, pyridylethyl or acetyl;

$R^6$ independently of the meaning of $R^5$ has the meanings indicated for $R^5$ or, if $R^5$ is hydrogen or methyl, is also cyclohexyl, 3-(2-ethoxyethoxy)propyl, benzyl which carries one or two chlorine atoms or the radical —$COR^{10}$ on the phenyl ring, $(C_1$–$C_5)$-alkanoyl, the radical —$COR^{10}$ or the radical —$(CH_2)_4$—$COR^{10}$;

$R^7$ is $(C_1$–$C_4)$-alkyl, benzyl, phenyl which is unsubstituted or substituted by chlorine, the radical —$COR^8$ or the radical —$CO$—$O$—$CO$—$(C_1$–$C_4)$-alkyl or naphthyl;

$R^8$ is hydroxyl, methoxy, amino or $R^{10}$;

$R^9$ is $(C_1$–$C_4)$-alkyl, hydroxymethyl, trifluoromethyl, $(C_1$–$C_2)$-alkoxy or $R^{11}$;

$R^{10}$ is the radical

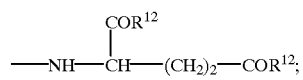

$R^{11}$ is the radical

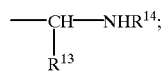

$R^{12}$ is hydroxyl or $(C_1-C_2)$-alkoxy;
$R^{13}$ is $(C_1-C_4)$-alkyl or benzyl;
$R^{14}$ is hydrogen or benzyloxycarbonyl;
and their tautomeric forms and their pharmacologically tolerable salts for the prevention and treatment of diseases which are caused by an increased nitric oxide level.

Alkyl groups can be straight-chain or branched. This also applies if they occur in other groups, for example in alkoxy, alkylmercapto, alkoxycarbonyl or alkanoyl groups. Examples of alkyl groups which can occur in the compounds of the formula I to be used according to the invention as such, i.e. as $(C_1-C_4)$- or $(C_1-C_{10})$-alkyl, or in other groups, are methyl, ethyl, n-propyl, i-propyl, n-butyl, i-butyl, sec-butyl, tert-butyl, n-pentyl, 3-methylbutyl, 2,2-dimethylpropyl, n-hexyl, n-heptyl, n-octyl, n-nonyl or n-decyl. Examples especially of $(C_1-C_5)$-alkanoyl are formyl, acetyl, propionyl, n-butyryl, i-butyryl, n-valeroyl, 3-methyl-n-butyryl or 2,2-dimethylpropionyl. Examples of $(C_1-C_2)$-alkoxy are methoxy and ethoxy.

A pyridyl radical can be a 2-pyridyl, 3-pyridyl or 4-pyridyl radical, preferably it is a 2-pyridyl radical. A phenyl radical which carries a substituent can carry this in the 2-, the 3- or the 4-position. The 3- and the 4-positions are preferred, the 4-position is particularly preferred. If the phenyl radical carries two substituents, these can be, for example, in the 2,3-, 2,4-,3,4- or 3,5-position. Preferably they are in the 2,4- or 3,4-position. A naphthyl radical can be a 1-naphthyl or 2-naphthyl radical; a 2-naphthyl radical is preferred. In phenylethyl and pyridylethyl radicals the phenyl or pyridyl radical can be in the 1-position or 2-position; it is preferably in the 2-position.

The compounds of the formula I can be present in various tautomeric forms and in various stereoisomeric forms. The present invention comprises not only the use of all tautomeric forms, but also that of all stereoisomeric forms, i.e., for example, that of pure enantiomers, of enantiomer mixtures and racemates, of pure diastereomers and diastereomer mixtures.

X is preferably O or NH.
Preferably, R is hydrogen.
$R^1$ is preferably hydrogen.
$R^2$ is preferably hydrogen. If $R^2$ is $(C_1-C_5)$-alkanoyl, acetyl, i-butyryl and pivaloyl are preferred.
$R^3$ is preferably $(C_1-C_{10})$-alkyloxy, phenyloxy, amino, methylamino, dimethylamino or the radical —$COR^{11}$. Particularly preferably, $R^3$ is $(C_5-C_{10})$-alkyloxy, amino or the radical —$COR^{11}$, where the $R^{14}$ contained in $R^{11}$ is benzyloxycarbonyl and the $R^{13}$ contained in $R^{11}$ is methyl, isopropyl or benzyl.

The compounds of the formula I are known and can be prepared according to or analogously to known processes. Known synthesis methods for pteridine derivatives of the formula I are, for example, the method of Gabriel-Isay or the Taylor method (see, for example, D. J. Brown, Fused Pyrimidines III, Pteridines (E. C. Taylor and A. Weissberger (Ed.), Wiley & Sons, New York)). In detail, the preparation of compounds of the formula I is described, for example, in EP-A-108 890, in the thesis of Hermann Michael Traub (Dissertation der Universität Konstanz, Deutschland (1987)), or in J. Med. Chem. 30 (1987), 40.

The compounds of the formula I to be used according to the invention can form salts with inorganic or organic acids. Suitable acids for the formation of pharmacologically acceptable acid addition salts are, for example: hydrochloric acid, hydrobromic acid, naphthalenedisulfonic acids, in particular 1,5-naphthalenedisulfonic acid, or phosphoric, nitric, sulfuric, oxalic, lactic, tartaric, acetic, salicylic, benzoic, formic, propionic, pivalic, diethylacetic, malonic, succinic, pimelic, fumaric, maleic, malic, sulfamic, phenylpropionic, gluconic, ascorbic, isonicotinic, methanesulfonic, p-toluenesulfonic, citric or adipic acid. The compounds of the formula I can add one or more acid equivalents. The acid addition salts can be prepared in the customary manner by combination of the components, expediently in a suitable solvent or diluent. Acid addition salts can be converted into one another by anion exchange. Compounds of the formula I which contain acidic groups can form salts with inorganic or organic bases. Examples of such salts are, for example, alkali metal salts, in particular sodium and potassium salts, or ammonium salts, in particular those with organic radicals on the ammonium nitrogen.

The inhibition of NO release by the compounds of the formula I can be determined by an activity assay based on the studies of Bredt and Snyder and also Schmidt et al. (see D. S. Bredt and S. S. Snyder, Isolation of nitric oxide synthase, a calmodulin-requiring enzyme, Proc. Natl. Acad. Sci. USA 87 (1990), 682; H. H. H. W. Schmidt et al., Purification of a soluble isoform of guanylyl cyclase-activating factor synthase, Proc. Natl. Acad. Sci. USA 88 (1991), 365). In this assay for purified NO synthase (NOS) the coproduct L-citrulline obtained during NO formation is determined quantitatively. This is carried out by the use of $^3$H-radiolabeled L-arginine as a substrate of the enzyme reaction, which is reacted to give $^3$H-L-citrulline and NO. After the enzyme incubation is complete, resulting L-citrulline is removed from unused L-arginine by means of ion-exchange chromatography of the reaction mixture; the $^3$H-activity determined by liquid scintillation measurement then corresponds to the amount of L-citrulline. Details of the procedure are given further below.

Diseases which arise due to an increased NO level and which can thus be treated according to the invention with the compounds of the formula I or which can be prevented using these, are, in particular, pathological blood pressure decreases, such as occur in septic or hemorrhagic shock, in tumor or cancer therapy with cytokines or in cirrhosis of the liver. In addition, inflammatory disorders, such as rheumatoid arthritis and in particular ulcerative colitis, as well as insulin-dependent diabetes mellitus and transplant rejection reactions.

However, the following disorders are also connected with increased production of nitric oxide and can be treated or prevented according to the invention. In the cardiovascular field, these are arteriosclerosis, post-ischemic tissue damage and infarct damage, reperfusion damage, myocarditis based on a Coxsackie virus infection and cardiomyopathy; in the nervous system/central nervous system field they are neuritides of varying etiogeneses (forms of neuritis), encephalomyelitides, viral neurodegenerative disorders, Alzheimer's disease, hyperalgesia, epilepsy and migraine, the treatment or prevention of Alzheimer's disease being excluded if $R^3$ in the formula I is hydroxyl; in the kidney field they are acute kidney failure and nephritides of varying etiogeneses, especially glomerulonephritis.

Additionally, treatments in the stomach and the uterus/placenta field and also affecting sperm motility are also fields of use for the compounds of the formula I.

The compounds of the formula I and their pharmacologically acceptable salts can be employed in research and in diagnostic processes as auxiliaries in biochemical and pharmacological studies, and they can be administered to animals, preferably to mammals, and in particular to humans, as therapeutics per se, as mixtures with one another or in the form of pharmaceutical preparations which allow enteral or parenteral use and which as active constituent contain an effective dose of at least one compound of the formula I or a salt thereof, in addition to customary pharmaceutically innocuous excipients and additives.

The therapeutics can be administered orally, e.g. in the form of pills, tablets, lacquered tablets, coated tablets, hard and soft gelatin capsules, solutions, syrups, emulsions or suspensions or aerosol mixtures. Administration, however, can also be carried out rectally, e.g. in the form of suppositories, or parenterally, e.g. in the form of injection solutions or infusion solutions, or percutaneously, e.g. in the form of ointments or tinctures.

In addition to the active compounds and excipients, the pharmaceutical preparations can also contain additives, such as, for example, fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants. They can also contain two or more compounds of the formula I or their pharmacologically acceptable salts and also other therapeutically active substances.

Other therapeutically active substances of this type are, for example: β-receptor blockers, such as, for example, propranolol, pindolol, metoprolol; vasodilators, such as, for example, carbocromene; tranquilizers, such as, for example, barbituric acid derivatives, 1,4-benzodiazepines and meprobamate; diuretics, such as, for example, chlorothiazide; cardiotonic agents, such as, for example, digitalis preparations; hypotensive agents, such as, for example, hydralazine, dihydralazine, ramipril, prazosin, clonidine, Rauwolfia alkaloids; agents which lower the fatty acid level in the blood, such as, for example, bezafibrate, fenofibrate; agents for thrombosis prophylaxis, such as, for example, phenprocoumon; anti-inflammatory substances, such as, for example, cortico-steroids, salicylates or propionic acid derivatives, such as, for example, ibuprofen; antibiotics, such as, for example, penicillins or cephalosporins; NO donors, such as, for example, organic nitrates or sydnone imines or furoxanes.

The dose can vary within wide limits and is to be suited to the individual conditions in each individual case. In general, a daily dose of approximately 0.5 to 100 mg, preferably 1 to 20 mg, per human individual is appropriate in the case of oral administration. In the case of other administration forms too, the daily dose is in similar ranges of amounts, i.e. in general likewise at 0.5 to 100 mg/person. The daily dose can be divided into several, e.g. 2 to 4, part administrations.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semisolid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

Until now, no pharmacological effects or medicinal uses were known for various pteridine derivatives of the formula I. For such compounds, the present invention gives the first medicinal indication. The present invention also relates to pteridine derivatives of the formula I

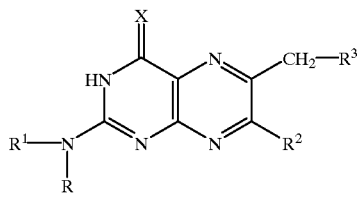

in which
X is O, NH or N—$(C_1$–$C_5)$-alkanoyl;
R is hydrogen and
$R^1$ is hydrogen or $(C_1$–$C_5)$-alkanoyl or R and $R^1$ together with the nitrogen atom to which they are bonded form a dimethylaminomethyleneamino group;
$R^2$ is hydrogen, methyl, phenyl, hydroxyl, methoxy or amino;
$R^3$ is the radical —$OR^4$, —$NR^5R^6$ or —$S(O)_mR^7$, where m is the numbers 0, 1 or 2;
$R^4$ is hydrogen, $(C_1$–$C_{10})$-alkyl, cyclohexyl, benzyl, phenyl which is unsubstituted or substituted by chlorine or the radical —$COR^8$, aminocarbonylmethyl which is unsubstituted or substituted on the nitrogen by one or two identical or different $(C_1$–$C_4)$-alkyl radicals, 2-methoxyethyl, the (2,2-dimethyl-1,3-dioxolan-4-yl) methyl radical or the radical —$COR^9$;
$R^5$ is hydrogen, methyl, ethyl, 2-hydroxyethyl, 2-chloroethyl, benzyl, pyridylmethyl, phenylethyl, pyridylethyl or acetyl;
$R^6$ independently of the meaning of $R^5$ has the meanings indicated for $R^5$ or, if $R^5$ is hydrogen or methyl, is also cyclohexyl, 3-(2-ethoxyethoxy)propyl, benzyl which carries one or two chlorine atoms or the radical —$COR^{10}$ on the phenyl ring, $(C_1$–$C_5)$-alkanoyl, the radical —$COR^{10}$ or the radical —$(CH_2)_4$—$COR^{10}$;
$R^7$ is $(C_1$–$C_4)$-alkyl, benzyl, phenyl which is unsubstituted or substituted by chlorine, the radical —$COR^8$ or the radical —CO—O—CO—$(C_1$–$C_4)$-alkyl or naphthyl;
$R^8$ is hydroxyl, methoxy, amino or $R^{10}$;
$R^9$ is $(C_1$–$C_4)$-alkyl, hydroxymethyl, trifluoromethyl, $(C_1$–$C_2)$-alkoxy or $R^{11}$;
$R^{10}$ is the radical

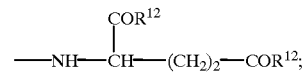

$R^{11}$ is the radical

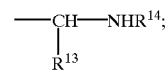

$R^{12}$ is hydroxyl or $(C_1$–$C_2)$-alkoxy;
$R^{13}$ is $(C_1$–$C_4)$-alkyl or benzyl;
$R^{14}$ is hydrogen or benzyloxycarbonyl;
and their tautomeric forms and also their pharmacologically tolerable salts where, however, compounds of the formula I in which $R^3$ is hydroxyl are excluded, as pharmacological active compounds. For preferred pteridine derivatives of this type, that stated above correspondingly applies.

The following examples give compounds of the formula I which can be employed according to the invention. In the examples the following abbreviations are used:

Me=methyl
Et=ethyl
iPr=isopropyl
iBu=isobutyl
tBu=tert-butyl
Ph=phenyl
Py=2-pyridyl
Z=benzyloxycarbonyl Ph-4-COOH, Ph-4-Cl and corresponding particulars are a phenyl radical which is substituted in the 4-position by the radical —COOH or by chlorine or by the group indicated in the particular example. $R^{10a}$, $R^{10b}$ and $R^{10c}$ are the radical of the formula

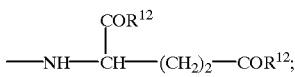

$$-\text{NH}-\underset{\underset{\text{COR}^{12}}{|}}{\text{CH}}-(\text{CH}_2)_2-\text{COR}^{12};$$

where in the case of $R^{10a}$ the radical $R^{12}$ is hydroxyl, in the case of $R^{10b}$ the radical $R^{12}$ is ethoxy and in the case of $R^{10c}$ the radical $R^{12}$ is methoxy.

$R^a$ is the (2,2-dimethyl-1,3-dioxolan-4-yl)methyl radical (D-form).

In Examples Nos. 1 to 109, R in the formula I is hydrogen.

| No. | X | $R^1$ | $R^2$ | $R^3$ |
|---|---|---|---|---|
| 1 | O | H | H | OH |
| 2 | O | tBuCO | H | OH |
| 3 | O | H | OH | OMe |
| 4 | O | H | H | OH |
| 5 | O | H | H | OEt |
| 6 | O | H | H | OiPr |
| 7 | O | H | H | OiBu |
| 8 | O | H | H | OtBu |
| 9 | O | H | H | OPh |
| 10 | O | H | H | O-(Ph-4-COOH) |
| 11 | O | H | H | O-(Ph-4-COOMe) |
| 12 | O | H | H | O-(Ph-4-COR$^{10a}$) |
| 13 | O | H | H | O-n-Octyl |
| 14 | O | H | H | O-n-Decyl |
| 15 | O | H | H | OCH$_2$CH$_2$OMe |
| 16 | O | H | H | OCOMe |
| 17 | O | MeCO | H | OCOMe |
| 18 | O | H | H | OCOtBu |
| 19 | O | tBuCO | H | OCOtBu |
| 20 | O | H | H | OCOCH$_2$OH |
| 21 | O | H | H | OCOCH(Me)-NHZ |
| 22 | O | H | H | OCOCH(iPr)—NHZ |
| 23 | O | H | H | OCOCH(CH$_2$Ph)-NHZ |
| 24 | O | H | H | OCOCF$_3$ |
| 25 | O | H | H | OCOOEt |
| 27 | O | H | H | NHMe |
| 28 | O | H | H | NMe$_2$ |
| 29 | O | H | H | NH—CH$_2$-(Ph-4-COR$^{10a}$) |
| 30 | O | H | H | NH—CH$_2$-(Ph-4-COR$^{10b}$) |
| 31 | O | tBuCO | H | N(Me)-CH$_2$CH$_2$-Py |
| 32 | O | tBuCO | H | N(CH$_2$CH$_2$-Py)$_2$ |
| 33 | O | tBuCO | H | N(CH$_2$-Py)$_2$ |
| 34 | O | H | H | N(CH$_2$CH$_2$—OH)$_2$ |
| 35 | O | H | H | N(CH$_2$CH$_2$—Cl)$_2$ |
| 36 | O | H | H | NH—COR$^{10a}$ |
| 37 | O | H | H | SMe |
| 38 | O | H | H | SEt |
| 39 | O | H | H | S-n-Propyl |
| 49 | O | H | H | S-n-Butyl |
| 41 | O | H | H | S-(Ph-4-CO—O—COiBu) |
| 42 | O | H | H | S-(Ph-4-COOH) |
| 43 | O | H | H | S-(Ph-4-COOMe) |
| 44 | O | H | H | S-(Ph-4-COR$^{10a}$) |
| 45 | O | H | H | S-(Ph-4-COR$^{10b}$) |
| 46 | O | H | H | S(O)$_2$Me |
| 47 | O | tBuCO | H | S(O)$_2$Me |
| 48 | NH | H | H | OH |
| 49 | NH | H | Me | OH |
| 50 | NH | H | OMe | OH |
| 51 | NH | H | OH | OH |
| 52 | NH | H | H | OMe |
| 53 | NH | H | H | OEt |
| 54 | NH | H | H | O-n-Propyl |
| 55 | NH | H | H | OiPr |
| 56 | NH | H | H | O-n-Butyl |
| 57 | NH | H | H | OiBu |
| 58 | NH | H | H | OtBu |
| 59 | NH | H | H | O-n-Octyl |
| 60 | NH | H | H | O-n-Decyl |
| 61 | NH | H | H | OCH$_2$CH$_2$OMe |
| 62 | NH | H | H | O-Cyclohexyl |
| 63 | NH | H | H | O—CH$_2$Ph |
| 64 | NH | H | H | OPh |
| 65 | NH | H | H | O-(Ph-4-Cl) |
| 66 | NH | H | H | O-(Ph-4-COOH) |
| 67 | NH | H | H | O-(Ph-4-CONH$_2$) |
| 68 | NH | H | H | O-(Ph-4-COR$^{10a}$) |
| 69 | NH | H | H | O-(Ph-4-COR$^{10b}$) |
| 70 | NH | H | H | O-R$^a$ |
| 71 | NH | H | H | OCOMe |
| 72 | NH | COMe | H | OCOMe |
| 73 | NH | H | H | OCOCH$_2$OH |
| 74 | NH | H | H | OCOCH(Me)-NHZ |
| 75 | NH | H | H | OCH$_2$CONEt$_2$ |
| 76 | NH | H | H | NH$_2$ |
| 77 | NH | H | H | NHMe |
| 78 | NH | H | H | NMe$_2$ |
| 79 | NH | H | NH$_2$ | NMe$_2$ |
| 80 | NH | H | H | NEt$_2$ |
| 81 | NH | H | H | NH—CH$_2$CH$_2$Ph |
| 82 | NH | H | H | NH—CH$_2$(Ph-4-COR$^{10a}$) |
| 83 | NH | H | H | NH—CH$_2$(Ph-4-COR$^{10b}$) |
| 84 | NH | H | H | N(Me)-(CH$_2$)$_4$—COR$^{10a}$ |
| 85 | NH | H | H | N(Me)-(CH$_2$)$_4$—COR$^{10b}$ |
| 86 | NH | H | H | N(Me)-(CH$_2$)$_4$—COR$^{10c}$ |
| 87 | NH | H | H | NH—CH$_2$-(2,4-Dichlorophenyl) |
| 88 | NH | H | H | NH—CH$_2$-(3,4-Dichlorophenyl) |
| 89 | NH | H | H | NH—(CH$_2$)$_3$—O—(CH$_2$)$_2$—OEt |
| 90 | NH | H | H | NH-Cyclohexyl |
| 91 | NH | H | H | N(CH$_2$CH$_2$—OH)$_2$ |
| 92 | NH | H | H | N(CH$_2$CH$_2$—Cl)$_2$ |
| 93 | NH | H | H | NH—COiPr |
| 94 | NH | H | H | SMe |
| 95 | NH | H | H | SCH$_2$Ph |
| 96 | NH | H | H | SPh |
| 97 | NH | H | H | S-(Ph-4-COOH) |
| 98 | NH | H | H | S-(Ph-4-COOMe) |
| 99 | NH | H | H | S-(Ph-4-COOEt) |
| 100 | NH | H | H | S-(Ph-4-Cl) |
| 101 | NH | H | H | S(O)-(Ph-4-Cl) |
| 102 | NH | H | H | S(O)$_2$-(Ph-4-Cl) |
| 103 | NH | H | H | S-(Ph-4-CO—O—COiBu) |
| 104 | NH | H | H | S-(Ph-4-COR$^{10a}$) |
| 105 | NH | H | H | S-(Ph-4-COR$^{10b}$) |
| 106 | NH | H | H | S-(2-Naphthyl) |
| 107 | NCOMe | MeCO | H | OCOMe |
| 108 | NCOMe | MeCO | H | N(COMe)$_2$ |
| 109 | NCOiPr | iPrCO | H | NH—COiPr |

Measurement of inhibition of the activity of purified nitric oxide synthase (NOS)

The coproduct L-citrulline obtained during the formation of NO by purified NOS is determined quantitatively in this activity assay. The substrate of the enzyme reaction employed is $^3$H-radiolabeled L-arginine, which is reacted to give $^3$H-L-citrulline and NO. After the enzyme incubation is complete, resulting L-citrulline is removed from unused L-arginine by means of ion-exchange chromatography of the reaction mixture; the $^3$H activity measured by liquid scintillation then corresponds to the amount of L-citrulline, which is a direct measure of the activity of NOS.

The base medium for carrying out the enzyme reaction is TE buffer (triethanolamine, EDTA, pH 7.0). The final volume of each incubation is 100 μl. The reaction mixture is obtained by mixing the following 6 components on ice:

1. "REA mix" (pH 7.0), which contains triethanolamine, calcium chloride, magnesium chloride, EDTA, L-arginine, calmodulin and flavine adenine dinucleotide (FAD);
2. freshly prepared stock solution of β-nicotinamide adenine dinucleotide phosphate, reduced form (NADPH);
3. (6R)-5,6,7,8-tetrahydro-L-biopterin dihydrochloride stock solution (BH$_4$) or —for experiments without BH$_4$ —TE buffer instead of this;
4. purified NO synthase from pig cerebellum or from pig liver;
5. L- [2,3,4,5-$^3$H]-arginine hydrochloride stock solution (1.5–2.6 TBq/mmol);
6. substance to be tested.

The final concentrations of the components in the incubation volume of 100 μl are:

Triethanolamine 50 mM, EDTA 0.5 mM, CaCl$_2$ 226 μM, MgCl$_2$ 477 μM, L-arginine 50 μM, calmodulin 0.5 μM, FAD 5 μM, NADPH 1 mM, BH$_4$ (if added) 2 μM, substance to be tested 100 μM. After mixing the components on ice the reaction mixture is immediately incubated in a water bath at 37° C. for 15 minutes. After this incubation time, the reaction is stopped by the addition of 900 μl of ice-cold "stop buffer" (20 mM sodium acetate, 2 mM EDTA, pH 5.5) and the mixture (total volume now 1.0 ml) is placed on ice. To separate off the unreacted $^3$H-L-arginine, the mixture is added to an ion-exchange column with 0.8 ml of Dowex AG 50 WX-8 (100–200 mesh), which was previously rinsed and equilibrated with 2 ml of stop buffer. After the application of the sample, the column is eluted twice with 1 ml of water each time. The runnings of the sample and the eluate are collected in scintillation containers and purified (total volume 3 ml). 9 ml of scintillator solution are added to the 3 ml aqueous measuring solution and the homogeneous mixture is measured for 1 minute per sample in a Tricarb 2500 TR (Packard) liquid scintillation counter. The activity found with the substance to be tested is given in percent of the activity of the control. Each substance is tested for antagonistic action at a concentration of 100 μM in the presence of 2 μM tetrahydrobiopterin and for agonistic action on the NOS in the absence of tetrahydrobiopterin. All incubations are set up in triplicate. Each experiment is repeated three times with various enzyme preparations. Some results are given in the following table.

| Compound of example | Enzyme from | Citrulline formation (% of the control) |
| --- | --- | --- |
| 1 | pig cerebellum | 61.7 |
| 21 | pig cerebellum | 60.8 |
| 23 | pig cerebellum | 2.5 |
| 37 | pig cerebellum | 22.9 |
| 60 | pig cerebellum | 26.2 |
| 76 | pig liver | 22.4 |

EXAMPLE A

Gelatin soft capsules, comprising 100 mg of active compound per capsule:

| | per capsule |
| --- | --- |
| Active compound | 100 mg |
| Triglyceride mixture fractionated from coconut fat | 400 mg |
| Capsule contents | 500 mg |

EXAMPLE B

Injection solution, comprising 2.0 mg of active compound per ml:

| | per ml |
| --- | --- |
| Active compound | 2.0 mg |
| Polyethylene glycol 400 | 5.0 mg |
| Sodium chloride | 2.7 mg |
| Water for injection purposes | to 1 ml |

EXAMPLE C

Emulsion, comprising 60 mg of active compound per 5 ml:

| | per 100 ml of emulsion |
| --- | --- |
| Active compound | 1.2 g |
| Neutral oil | q.s. |
| Sodium carboxymethylcellulose | 0.6 g |
| Polyoxyethylene stearate | q.s. |
| Glycerol, pure | 0.2 to 2.0 g |
| Flavoring | q.s. |
| Water (demineralized or distilled) | to 100 ml |

EXAMPLE D

Rectal pharmaceutical form, comprising 40 mg of active compound per suppository:

| | per suppository |
| --- | --- |
| Active compound | 40 mg |
| Suppository base mass | to 2 g |

EXAMPLE E

Tablets, comprising 40 mg of active compound per tablet:

|  | per tablet |
|---|---|
| Active compound | 40 mg |
| Lactose | 600 mg |
| Corn starch | 300 mg |
| Soluble starch | 20 mg |
| Magnesium stearate | 40 mg |
|  | 1000 mg |

EXAMPLE F

Coated tablets, comprising 50 mg of active compound per coated tablet:

|  | per coated tablet |
|---|---|
| Active compound | 50 mg |
| Corn starch | 100 mg |
| Lactose | 60 mg |
| sec. calcium phosphate | 30 mg |
| Soluble starch | 5 mg |
| Magnesium stearate | 10 mg |
| Colloidal silicic acid | 5 mg |
|  | 260 mg |

EXAMPLE G

For the preparation of the contents of hard gelatin capsules, the following recipes are suitable:

| a) | Active compound | 100 mg |
|---|---|---|
|  | Corn starch | 300 mg |
|  |  | 400 mg |
| b) | Active compound | 140 mg |
|  | Milk sugar | 180 mg |
|  | Corn starch | 180 mg |
|  |  | 500 mg |

EXAMPLE H

Drops can be prepared according to the following recipe (100 mg of active compound in 1 ml=20 drops):

| Active compound | 10 g |
|---|---|
| Methyl benzoate | 0.07 g |
| Ethyl benzoate | 0.03 g |
| Ethanol, 96% strength | 5 ml |
| Demineralized water | to 100 ml |

We claim:

1. A method for the treatment of a disease associated with an increased nitric oxide level which comprises administering to a mammal in need of such treatment an effective amount of a pteridine derivative of the formula

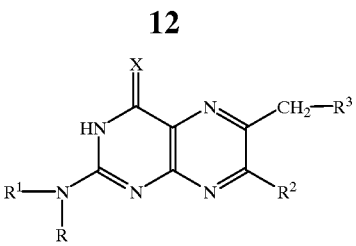

in which

X is O, NH or N—$(C_1-C_5)$-alkanoyl;

R is hydrogen and $R^1$ is hydrogen or $(C_1-C_5)$-alkanoyl or R and $R^1$ together with the nitrogen atom to which they are bonded from a dimethylaminomethyleneamino group;

$R^2$ is hydrogen, methyl, phenyl, hydroxyl, methoxy or amino;

$R^3$ is the radical —$OR^4$, —$NR^5R^6$ or —$S(O)_mR^7$, where m is the numbers 0, 1 or 2;

$R^4$ is hydrogen, $(C_1-C_{10})$-alkyl, cyclohexyl, benzyl, phenyl which is unsubstituted or substituted by chlorine or the radical —$COR_8$, aminocarbonylmethyl which is unsubstituted or substituted on the nitrogen by one or two identical or different $(C_1-C_4)$-alkyl radicals, 2-methoxyethyl, the (2,2-dimethyl-1,3-dioxolan-4-yl) methyl radical or the radical —$COR^9$;

$R^5$ is hydrogen, methyl, ethyl, 2-hydroxyethyl, 2-chloroethyl, benzyl, pyridylmethyl, phenylethyl, pyridylethyl or acetyl;

$R^6$ independently of the meaning of $R^5$ has the meanings indicated for $R^5$ or, if $R^5$ is hydrogen or methyl, is also cyclohexyl, 3-(2-ethoxyethoxy)-propyl, benzyl which carries one or two chlorine atoms or the radical —$COR^{10}$ on the phenyl ring, $(C_1-C_5)$-alkanoyl, the radical —$COR^{10}$ or the radical —$(CH_2)_4$—$COR^{10}$;

$R^7$ is $(C_1-C_4)$-alkyl, benzyl, phenyl which is unsubstituted or substituted by chlorine, the radical —$COR^8$ or the radical —CO—O—CO—$(C_1-C_4)$-alkyl or naphthyl;

$R^8$ is hydrogen, methoxy, amino or $R^{10}$;

$R^9$ is $(C_1-C_4)$-alkyl, hydroxymethyl, trifluoromethyl, $(C_1-C_2)$-alkoxy or $R^{11}$;

$R^{10}$ is the radical

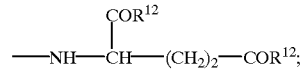

$R^{11}$ is the radical

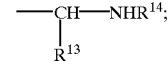

$R^{12}$ is hydroxyl or $(C_1-C_2)$-alkoxy;

$R^{13}$ is $(C_1-C_4)$-alkyl or benzyl;

$R''^{14}$ is hydrogen or benzyloxycarbonyl;

and their tautomeric forms and their pharmacologically tolerable salts.

2. A method as claimed in claim 1, wherein R is hydrogen and X is O or NH.

3. A method as claimed in claim 1, wherein $R_1$ and/or $R^2$ is hydrogen.

4. A method as claimed in claim 1, wherein $R^3$ is $(C_1-C_{10})$-alkyloxy, phenyloxy, amino, methylamino, dimethylamino or the radical —$OCOR^{11}$.

5. A method as claimed in claim 1 for the treatment of disorders of the nervous system selected from the group consisting of Alzheimer's disease, epilepsy and migraine.

6. A method for the inhibition of nitric oxide production in a mammal, comprising administering to a mammal in need of such inhibition an inhibitory effective amount of a pteridine derivative of the formula I

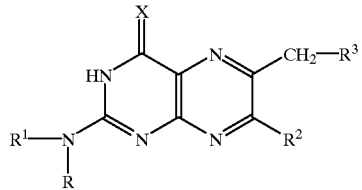

(I)

in which

X is O, NH or N—$(C_1$–$C_5)$-alkanoyl;

R is hydrogen and $R_1$ is hydrogen or $(C_1$–$C_5)$-alkanoyl or R and $R^1$ together with the nitrogen atom to which they are bonded from a dimethylaminomethyleneamino group;

$R^2$ is hydrogen, methyl, phenyl, hydroxyl, methoxy or amino;

$R^3$ is the radical —$OR^4$, —$NR^5R^6$ or —$S(O)_mR^7$, where m is the numbers 0, 1 or 2;

$R^4$ is $(C_1$–$C_{10})$-alkyl, cyclohexyl, benzyl, phenyl which is unsubstituted or substituted by chlorine or the radical —$COR^8$, aminocarbonylmethyl which is unsubstituted or substituted on the nitrogen by one or two identical or different $(C_1$–$C_4)$-alkyl radicals, 2-methoxyethyl, the (2,2-d imethyl-1,3-dioxolan-4-yl)methyl radical or the radical —$COR^9$;

$R^5$ is hydrogen, methyl, ethyl, 2-hydroxyethyl, 2-chloroethyl, benzyl, pyridylmethyl, phenylethyl, pyridylethyl or acetyl;

$R^6$ independently of the meaning of $R^5$ has the meanings indicated for $R^5$ or, if $R^5$ is hydrogen or methyl, is also cyclohexyl, 3-(2-ethoxyethoxy)-propyl, benzyl which carries one or two chlorine atoms or the radical —$COR^{10}$ on the phenyl ring, $(C_1$–$C_5)$ -alkanoyl, the radical —$COR^{10}$ or the radical —$(CH_2)_4$—$COR^{10}$;

$R^7$ is $(C_1$–$C_4)$-alkyl, benzyl, phenyl which is unsubstituted or substituted by chlorine, the radical —$COR^8$ or the radical —CO—O—CO—$(C_1$–$C_4)$-alkyl or naphthyl;

$R^8$ is hydrogen, methoxy, amino or $R^{10}$;

$R^9$ is $(C_1$–$C_4)$-alkyl, hydroxymethyl, trifluoromethyl, $(C_1$–$C_2)$-alkoxy or $R^{11}$;

$R^{10}$ is the radical

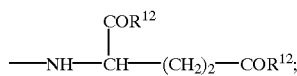

$R^{11}$ is the radical

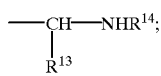

$R^{12}$ is hydroxyl or $(C_1$–$C_2)$-alkoxy;

$R^{13}$ is $(C_1$–$C_4)$-alkyl or benzyl;

$R^{14}$ is hydrogen or benzyloxycarbonyl;

or a tautomeric form or a pharmacologically tolerable salt thereof.

7. A method for the treatment of a pathological blood pressure decrease due to increased levels of nitric oxide production in a mammal, comprising administering to a mammal in need of such treatment an inhibitory effective amount of a pteridine derivative of the formula I

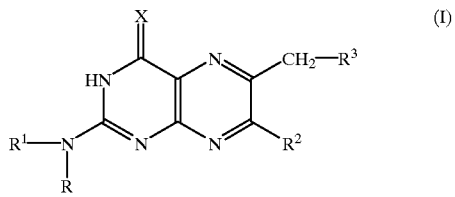

(I)

in which

X is O, NH or N—$(C_1$–$C_5)$-alkanoyl;

R is hydrogen and $R^1$ is hydrogen or $(C_1$–$C_5)$-alkanoyl or R and $R^1$ together with the nitrogen atom to which they are bonded from a dimethylaminomethyleneamino group;

$R^2$ is hydrogen, methyl, phenyl, hydroxyl, methoxy or amino;

$R^3$ is the radical —$OR^4$, —$NR^5R^6$ or —$S(O)_mR^7$, where m is the numbers 0, 1 or 2;

$R^4$ is hydrogen, $(C_1$–$C_{10})$-alkyl, cyclohexyl, benzyl, phenyl which is unsubstituted or substituted by chlorine or the radical —$COR^8$, aminocarbonylmethyl which is unsubstituted or substituted on the nitrogen by one or two identical or different $(C_1$–$C_4)$-alkyl radicals, 2-methoxyethyl, the (2,2-dimethyl-1,3-dioxolan-4-yl) methyl radical or the radical —$COR^9$;

$R^5$ is hydrogen, methyl, ethyl, 2-hydroxyethyl, 2-chloroethyl, benzyl, pyridylmethyl, phenylethyl, pyridylethyl or acetyl;

$R^6$ independently of the meaning of $R^5$ has the meanings indicated for $R^5$ or, if $R^5$ is hydrogen or methyl, is also cyclohexyl, 3-(2-ethoxyethoxy)-propyl, benzyl which carries one or two chlorine atoms or the radical —$COR^{10}$ on the phenyl ring, $(C_1$–$C_5)$-alkanoyl, the radical —$COR^{10}$ or the radical —$(CH_2)_4$—$COR^{10}$;

$R^7$ is $(C_1$–$C_4)$-alkyl, benzyl, phenyl which is unsubstituted or substituted by chlorine, the radical —$COR^8$or the radical —CO—O—CO—$(C_1$–$C_4)$-alkyl or naphthyl;

$R^8$ is hydrogen, methoxy, amino or $R^{10}$;

$R^9$ is $(C_1$–$C_4)$-alkyl, hydroxymethyl, trifluoromethyl, $(C_1$–$C_2)$-alkoxy or $R^{11}$;

$R^{10}$ is the radical

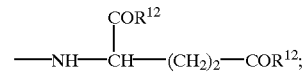

$R^{11}$ is the radical

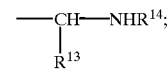

$R^{12}$ is hydroxyl or $(C_1$–$C_2)$-alkoxy;

$R^{13}$ is $(C_1$–$C_4)$-alkyl or benzyl;

$R^{14}$ is hydrogen or benzyloxycarbonyl; or a tautomeric form or a pharmacologically tolerable salt thereof.

8. The method of claim 7, wherein the pathological blood pressure decrease is due to septic shock.

9. The method of claim 7, wherein the pathological blood pressure decrease is due to tumor therapy with cytokines.

10. A method for the treatment of an inflammatory disorder due to increased levels of nitric oxide production in a mammal, comprising administering to a mammal in need of such treatment an inhibitory effective amount of a pteridine derivative of the Formula I

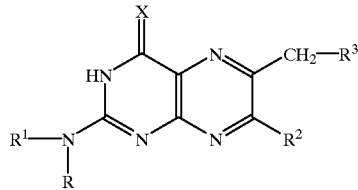
(I)

in which

X is O, NH or N—($C_1$–$C_5$)-alkanoyl;

R is hydrogen and $R^1$ is hydrogen or ($C_1$–$C_5$)-alkanoyl or R and $R^1$ together with the nitrogen atom to which they are bonded from a dimethylaminomethyleneamino group;

$R^2$ is hydrogen, methyl, phenyl, hydroxyl, methoxy or amino;

$R^3$ is the radical —$OR^4$, —$NR^5R^6$ or —$S(O)_mR^7$, where m is the numbers 0, 1 or 2;

$R^4$ is hydrogen, ($C_1$–$C_{10}$)-alkyl, cyclohexyl, benzyl, phenyl which is unsubstituted or substituted by chlorine or the radical —$COR^8$, aminocarbonylmethyl which is unsubstituted or substituted on the nitrogen by one or two identical or different ($C_1$–$C_4$)-alkyl radicals, 2-methoxyethyl, the (2,2-dimethyl-1,3-dioxolan-4-yl) methyl radical or the radical —$COR^9$;

$R^5$ is hydrogen, methyl, ethyl, 2-hydroxyethyl, 2-chloroethyl, benzyl, pyridylmethyl, phenylethyl, pyridylethyl or acetyl;

$R^6$ independently of the meaning of $R^5$ has the meanings indicated for $R^5$ or, if $R^5$ is hydrogen or methyl, is also cyclohexyl, 3-(2-ethoxyethoxy)-propyl, benzyl which carries one or two chlorine atoms or the radical —$COR^{10}$ on the phenyl ring, ($C_1$–$C_5$)-alkanoyl, the radical —$COR^{10}$ or the radical —$(CH_2)_4$—$COR^{10}$;

$R^7$ is ($C_1$–$C_4$)-alkyl, benzyl, phenyl which is unsubstituted or substituted by chlorine, the radical —$COR^8$ or the radical —CO—O—CO—($C_1$–$C_4$)-alkyl or naphthyl;

$R^8$ is hydrogen, methoxy, amino or $R^{10}$;

$R^9$ is ($C_1$–$C_4$)-alkyl, hydroxymethyl, trifluoromethyl, ($C_1$–$C_2$)-alkoxy or $R^{11}$;

$R^{10}$ is the radical

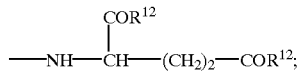

$R^{11}$ is the radical

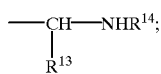

$R^{12}$ is hydroxyl or ($C_1$–$C_2$)-alkoxy;

$R^{13}$ is ($C_1$–$C_4$)-alkyl or benzyl;

$R^{14}$ is hydrogen or benzyloxycarbonyl;

or a tautomeric form or a pharmacologically tolerable salt thereof.

11. The method of claims 10, wherein the inflammatory disorder is ulcerative colitis.

12. A method for the treatment of a disease associated with infarct damage and/or reperfusion damage due to increased levels of nitric oxide production in a mammal, comprising administering to a mammal in need of such treatment an inhibitory effective amount of a pteridine derivative of the formula I

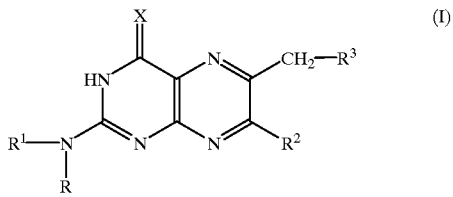
(I)

in which x is O, NH or N—($C_1$–$C_5$)-alkanoyl;

R is hydrogen and $R^1$ is hydrogen or ($C_1$–$C_5$)-alkanoyl or R and $R^1$ together with the nitrogen atom to which they are bonded from a dimethylaminomethyleneamino group;

$R^2$ is hydrogen, methyl, phenyl, hydroxyl, methoxy or amino;

$R^3$ is the radical —$OR^4$, —$NR^5R^6$ or —$S(O)_mR^7$, where m is the numbers 0, 1 or 2;

$R^4$ is hydrogen, ($C_1$–$C_{10}$)-alkyl, cyclohexyl, benzyl, phenyl which is unsubstituted or substituted by chlorine or the radical —$COR^8$, aminocarbonylmethyl which is unsubstituted or substituted on the nitrogen by one or two identical or different ($C_1$–$C_4$)-alkyl radicals, 2-methoxyethyl, the (2,2-dimethyl-1,3-dioxolan-4-yl) methyl radical or the radical —$COR^9$;

$R^5$ is hydrogen, methyl, ethyl, 2-hydroxyethyl, 2-chloroethyl, benzyl, pyridylmethyl, phenylethyl, pyridylethyl or acetyl;

$R^6$ independently of the meaning of $R^5$ has the meanings indicated for $R^5$ or, if $R^5$ is hydrogen or methyl, is also cyclohexyl, 3-(2-ethoxyethoxy)-propyl, benzyl which carries one or two chlorine atoms or the radical —$COR^{10}$ on the phenyl ring, ($C_1$–$C_5$)-alkanoyl, the radical —$COR^{10}$ or the radical —$(CH_2)_4$—$COR^{10}$;

$R^7$ is ($C_1$–$C_4$)-alkyl, benzyl, phenyl which is unsubstituted or substituted by chlorine, the radical —$COR^8$ or the radical —CO—O—CO—($C_1$–$C_4$)-alkyl or naphthyl;

$R^8$ is hydrogen, methoxy, amino or $R^{10}$;

$R^9$ is ($C_1$–$C_4$)-alkyl, hydroxymethyl, trifluoromethyl, ($C_1$–$C_2$)-alkoxy or $R^{11}$;

$R^{10}$ is the radical

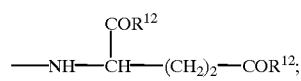

$R^{11}$ is the radical

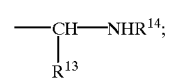

$R^{12}$ is hydroxyl or ($C_1$–$C_2$)-alkoxy;

$R^{13}$ is ($C_1$–$C_4$)-alkyl or benzyl;

$R^{14}$ is hydrogen or benzyloxycarbonyl;

or a tautomeric form or a pharmacologically tolerable salt thereof.

13. A method for the treatment of transplant rejection reactions due to increased levels of nitric oxide production in a mammal, comprising administering to a mammal in need of such treatment an inhibitory effective amount of a pteridine derivative of the formula I

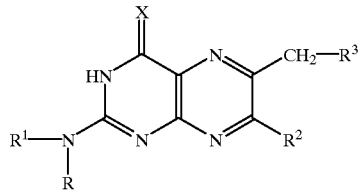

in which

X is O, NH or N—$(C_1-C_5)$-alkanoyl;

R is hydrogen and $R^1$ is hydrogen or $(C_1-C_5)$-alkanoyl or R and $R^1$ together with the nitrogen atom to which they are bonded from a dimethylaminomethyleneamino group;

$R^2$ is hydrogen, methyl, phenyl, hydroxyl, methoxy or amino;

$R^3$ is the radical —$OR^4$, —$NR^5R^6$ or —$S(O)_mR^7$, where m is the numbers 0, 1 or 2;

$R^4$ is hydrogen, $(C_1-C_{10})$-alkyl, cyclohexyl, benzyl, phenyl which is unsubstituted or substituted by chlorine or the radical —$COR^8$, aminocarbonylmethyl which is unsubstituted or substituted on the nitrogen by one or two identical or different $(C_1-C_4)$-alkyl radicals, 2-methoxyethyl, the (2,2-dimethyl-1,3-dioxolan-4-yl)methyl radical or the radical —$COR^9$;

$R^5$ is hydrogen, methyl, ethyl, 2-hydroxyethyl, 2-chloroethyl, benzyl, pyridylmethyl, phenylethyl, pyridylethyl or acetyl;

$R^6$ independently of the meaning of $R^5$ has the meanings indicated for $R^5$ or, if $R^5$ is hydrogen or methyl, is also cyclohexyl, 3-(2-ethoxyethoxy)-propyl, benzyl which carries one or two chlorine atoms or the radical —$COR^{10}$ on the phenyl ring, $(C_1-C_5)$-alkanoyl, the radical —$COR^{10}$ or the radical —$(CH_2)_4$—$COR^{10}$;

$R^7$ is $(C_1-C_4)$-alkyl, benzyl, phenyl which is unsubstituted or substituted by chlorine, the radical —$COR^8$ or the radical —CO—O—CO—$(C_1-C_4)$-alkyl or naphthyl;

$R^8$ is hydrogen, methoxy, amino or $R^{10}$;

$R^9$ is $(C_1-C_4)$-alkyl, hydroxymethyl, trifluoromethyl, $(C_1-C_2)$-alkoxy or $R^{11}$;

$R^{10}$ is the radical

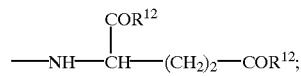

$R^{11}$ is the radical

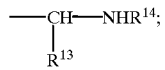

$R^{12}$ is hydroxyl or $(C_1-C_2)$-alkoxy;

$R^{13}$ is $(C_1-C_4)$-alkyl or benzyl;

$R^{14}$ is hydrogen or benzyloxycarbonyl;

or a tautomeric form or a pharmacologically tolerable salt thereof.

\* \* \* \* \*

UNITED STATES PATENT AND TRADEMARK OFFICE
CERTIFICATE OF CORRECTION

PATENT NO. : 5,902,810
DATED : May 11, 1999
INVENTOR(S) : Pfleiderer et al.

It is certified that error appears in the above-identified patent and that said Letters Patent is hereby corrected as shown below:

Title Page, Item [75], in the Inventors, line 1, "Konstantz:"
should read --Konstanz--.
Title Page, Item [57], in the Abstract, line 4, "N-($C_{1-C5}$)-alkanoyl"
should read --N-($C_1$-$C_5$)-alkanoyl--.
Claim 1, col.12, line 14, "from" should read --form--.
Claim 1, col. 12, line 21, after "$R^4$ is" delete "hydrogen,".
Claim 1, col. 12, line 23, "-$COR_8$" should read -- -$COR^8$--.
Claim 1, col.12, line 58, "$R^{n14}$" should read --$R^{14}$--.
Claim 3, col.12, line 63, "$R_1$," should read --$R^1$--.
Claim 4, col 12, line 65, "$R^3$is" should read --$R^3$ is --.
Claim 6, col. 13, line 20, "$R_1$," should read --$R^1$--.
Claim 6, col. 13, line 21, "from" should read --form--.
Claim 6, col. 13, line 33, "(2,2-d imethyl-1"
should read --(2,2-dimethyl-1--.

UNITED STATES PATENT AND TRADEMARK OFFICE
CERTIFICATE OF CORRECTION

PATENT NO. : 5,902,810
DATED : May 11, 1999
INVENTOR(S) : Pfleiderer et al.

It is certified that error appears in the above-identified patent and that said Letters Patent is hereby corrected as shown below:

Claim 7, col. 14, line 19, "from" should read --form--.
Claim 7, col. 14, line 44, "-COR$^8$or" should read -- -COR$^8$ or--.
Claim 10, col. 15, line 7, "Formula" should read --formula--.
Claim 10, col. 15, line 21, "from" should read --form--.
Claim 11, col. 16, line 1, "claims 10" should read --claim 10--.
Claim 12, col. 16, line 22, "from" should read --form--.

Signed and Sealed this

Fourth Day of January, 2000

Attest:

Attesting Officer

*Acting Commissioner of Patents and Trademarks*